United States Patent [19]
Lloyd

[11] Patent Number: 4,475,908
[45] Date of Patent: Oct. 9, 1984

[54] OSTOMY DEVICES

[76] Inventor: Ronald Lloyd, 63 Cambridge Rd., Sawbridgeworth, Hertfordshire, England

[21] Appl. No.: 290,160

[22] Filed: Aug. 5, 1981

[30] Foreign Application Priority Data

Aug. 7, 1980 [GB] United Kingdom ............... 8025827

[51] Int. Cl.³ .............................................. A61F 5/44
[52] U.S. Cl. .................................... 604/339; 604/344
[58] Field of Search ............... 128/156, 283; 604/355, 604/356, 357, 332, 338–339, 342, 344

[56] References Cited

U.S. PATENT DOCUMENTS 3,713,445 1/1973 Marsan ................................ 128/283
3,972,328 8/1976 Chen .................................... 128/156
3,973,563 8/1976 Green et al. ........................ 128/156
3,975,567 8/1976 Lock .................................... 128/156
4,024,312 5/1977 Korpman ............................ 128/156
4,213,458 7/1980 Nolan et al. ........................ 128/283
4,340,043 7/1982 Seymour ............................ 128/156

Primary Examiner—C. Fred Rosenbaum

[57] ABSTRACT

An adhesive mount for adhesively attaching an ostomy bag about the stoma of a patient which comprises a layer of moisture vapor transmitting plastics foam and a layer of moisture vapor transmitting pressure sensitive adhesive in juxtaposition therewith and an ostomy bag device having an adhesive mount bonded about an aperture thereof is described.

5 Claims, 3 Drawing Figures

OSTOMY DEVICES

This invention is concerned with improvements in and relating to ostomy pouches or bags, that is bags or pouches adapted to receive the drainage from the stoma of a patient who has undergone a colostomy or like operation.

One important problem which arises in connection with ostomy pouches is that of their attachment to the patient and this is commonly achieved by providing the bag with a mounting device comprising a patch surrounding the stoma-receiving aperture in the bag which mount has on the face thereof remote from the bag a layer of a pressure sensitive adhesive. Since the patient is obliged to wear a bag at almost all times, problems of irritation can arise in the area of skin surrounding the stoma and, in order to alleviate this problem, it is an object of the present invention to provide an improved adhesive mount which permits the skin in contact to "breathe".

In one aspect the invention provides an adhesive mount for adhesively attaching an ostomy bag about the stoma of a patient which comprises a layer of moisture vapour transmitting plastics foam and a layer of moisture vapour transmitting pressure sensitive adhesive in juxtaposition therewith.

In another aspect the invention provides an ostomy bag device which comprises an ostomy bag having an aperture adapted to receive the stoma of a patient, an apertured adhesive mount bonded to the bag about said aperture, said adhesive mount comprising a layer of a moisture vapour transmitting plastics foam and a layer of a moisture vapour transmitting pressure sensitive adhesive.

The moisture vapour transmitting foam is preferably a reticulated foam. Such reticulated foams may aptly be made of polyurethane. One source of flexible polyurethane reticulated foams is Scott Foam Division, Scott Paper Company, 1500E Second Street, Chester PA 19013, USA.

In order that the invention may be well-understood reference will now be made to the accompanying drawings in which.

Figure 1:
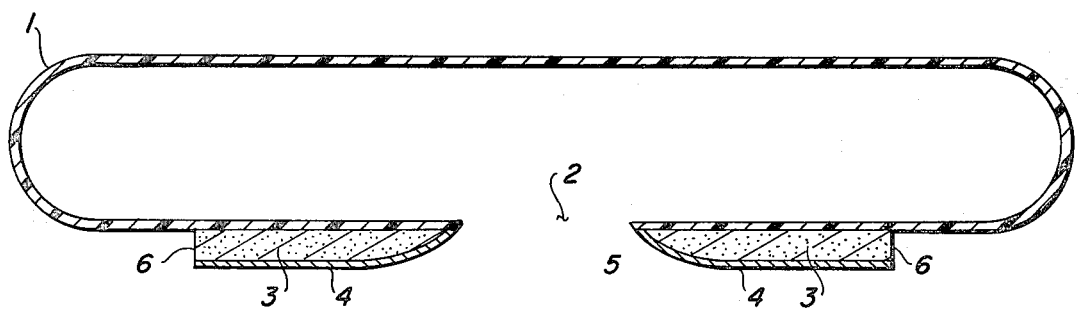
FIG. 1 is a diagrammatic cross-section through a first embodiment of ostomy device according to the invention.

As shown in FIG. 1, an ostomy device according to the invention basically comprises a bag 1, generally formed of flexible film plastics material such as polyethylene, polypropylene or polyvinylidene chloride, having an aperture 2, and an adhesive mount consisting of a layer of moisture vapour transmitting material 3 bonded to the bag 1 around the aperture 2 and is provided in its outer or skin engaging surface with a layer of moisture vapour transmitting pressure-sensitive adhesive 4. The inner margin 5, of layer 3, is sealed to bag 1 and the outer margin thereof, 6, is open or unsealed.

Layer 3 of the adhesive mount is formed of moisture vapour transmitting foam and thus has an open structure capable of transmitting moisture vapor so that, in use, moisture vapor may pass, from the skin of the user, through layer 4 into layer 3 and out through outer unsealed margin 6. Suitable materials for forming layer 3 include, for example, open celled plastics foams and reticulated plastics foams. The function of layer 3 is basically to act as a vapour conductive spacer between the bag 1 and moisture vapour transmitting adhesive layer 4 or skin to which the adhesive layer is in contact when the adhesive mount is in use.

To this end layer 3 is desirably formed of as open a structure as possible. Reticulated plastics foams being especially preferred. It may often be desirable that layer 3 be formed of a resilient or elastic foam in order that a patient may, to relieve irritation, 'pump' the adhesive mount to induce passage of air therethrough, and also in order to permit accommodation of natural movement of the skin. Preferably, layer 3 has a thickness of from 2 to 5 mm, preferably from 2 to 4 mm.

Layer 3 of the adhesive mount may be bonded to bag 1 by means of an adhesive, e.g. a pressure-sensitive adhesive, and it is, of course, not necessary that this adhesive be moisture transmitting since it is in contact with the moisture impervious wall of bag 1. Alternatively, layer 3 of the adhesive mount may be welded to bag 1 either by spot or continuous welds. It is preferred that the margin 5 of layer 3 of the adhesive mount is continuously bonded to bag 1. Finally, layer 3 of the adhesive mount may be formed integrally with the wall of bag 1.

It is essential that the pressure sensitive adhesive layer 4 be moisture vapour transmitting and this may be achieved in a variety of manners. Thus, for example, layer 4 may take the form of a continuous layer of a pressure sensitive adhesive which is in itself moisture vapour transmitting, e.g. a polyvinyl ethyl ether adhesive as described in BP No. 1,280,631. Alternatively the adhesive layer may be microporous or macroporous in nature or may be applied to the surface of adhesive mount in a patterned manner.

If layer 3 is of a very open nature it may prove difficult to support a continuous or substantially continuous layer of adhesive thereon and in this case the adhesive may be supported on a moisture vapour transmitting support, such as plastics net, in turn bonded to layer 3, for example by means of an adhesive which will, of course, also have to be moisture vapour transmitting. Alternatively layer 3 may be formed with a skin or adhesive supporting face of smaller pore size than the body of layer 3 it being appreciated that any such face will also be moisture vapour transmitting. Such a layer of the adhesive mount may be formed, for example, by casting a suitable foam onto a porous net or non-woven fabric support.

It is preferred in the bag of the invention that the inner margin 5 of layer 3 of adhesive mount be sealed, that is that the inner margin of adhesive layer 4 seal with the wall of bag 1 in order to prevent in-use dissemination of odour from bag 1 through layer 3. It is equally important that the outer margin of layer 3 of the adhesive mount be unsealed to permit the exit of moisture vapour from layer 3.

Figure 2:
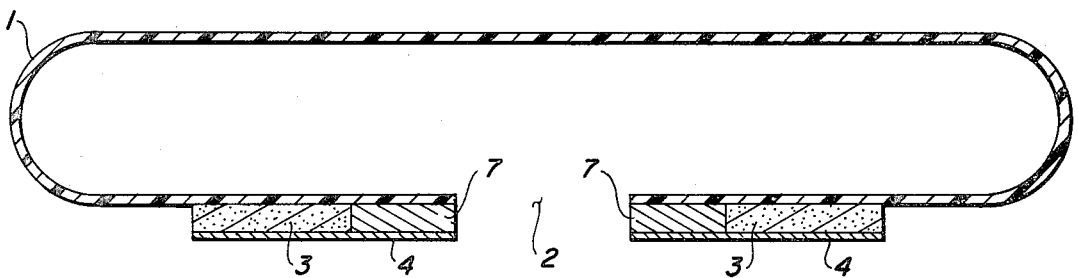
FIG. 2 is a diagrammatic cross-section through another embodiment of ostomy device according to the invention.

In order to reduce the possibility of dissemination of odour from the bag the inner margin of aperture 2 may be provided with a sealing ring made of impervious material such as karaya gum. Such an embodiment as shown in FIG. 2 of the drawing in which the sealing ring is shown at 7.

Further odour control may be achieved by providing in or on the surface of layer 3, an odour absorbent material such as absorbent carbon or an absorbent silicate.

Prior to use, the outer adhesive layer 4 will, as is conventional, be provided with a removable protective layer, for example of release coated paper, and this will be removed to expose the adhesive layer prior to application to the skin.

The adhesive mount can be in the form of roll, as continuous strips or as individual pieces e.g. discs of suitable dimensions to fit the requirements of a patient.

Figure 3:
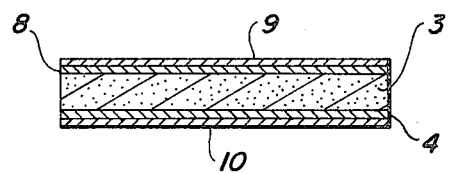
FIG. 3 is a diagrammatic cross-section through an adhesive mount for use in the manufacture of an ostomy device according to the invention.

One form of the adhesive mount of the invention is illustrated in FIG. 3 of the drawings and comprising a layer of moisture vapour transmitting foam 3 of a reticulated plastics foam having on one face thereof a first adhesive layer 8 covered with a protective cover 9 and on the opposite face a second adhesive layer 4 of a moisture vapour transmitting adhesive covered with a protective layer 10. Adhesive layer 8 need not be of a moisture transmitting nature and indeed often will not. Either or both of adhesive layers 4 and 8 may be supported on support layer as discussed above, it being appreciated that in this case any support layer covering adhesive layer 8 need not be moisture vapour transmitting.

The adhesive mount is then perforated or cut to provide an aperture therein for example corresponding to aperture 2 with if required sealing of the margin of the aperture. Protective cover 9 is then removed from adhesive layer 8 to expose adhesive 8 surface and the perforated adhesive mount then bonded to the colostomy bag by means of adhesive 8 to surround the aperture therein.

When used herein the term "in juxtaposition" means laying adjacent to. The term includes the preferred meaning of in contact with over a major face, for example where two layers are in direct contact with one another.

What we claim is:

1. An ostomy bag device which comprises an ostomy bag having an aperture adapted to receive the stoma of a patient, an apertured adhesive mount bonded to the bag about said aperture, said adhesive mount comprising a layer of a moisture vapour transmitting plastics foam and a layer of a moisture vapour transmitting pressure sensitive adhesive.

2. An ostomy bag device as claimed in claim 1 in which the moisture vapour transmitting foam comprises a polyurethane.

3. An ostomy bag device as claimed in claim 1 in which the moisture vapour transmitting plastics foam is a reticulated foam.

4. An ostomy bag device as claimed in claim 1 in which the moisture vapour transmitting adhesive layer is continuous.

5. An ostomy bag device as claimed in claim 2 in which the continuous adhesive layer comprises a polyvinyl ethyl ether.

* * * * *